United States Patent [19]

Brepoels et al.

[11] 4,145,362

[45] Mar. 20, 1979

[54] PROCESS FOR THE ARYLATION OF OLEFINES

[75] Inventors: Joseph R. Brepoels, Beverloo; Jean-Marie Vaneghem, Balen, both of Belgium

[73] Assignee: S.A. P R B en Neerlandais PRB N.V., Brussels, Belgium

[21] Appl. No.: 795,544

[22] Filed: May 10, 1977

Related U.S. Application Data

[63] Continuation of Ser. No. 345,197, Mar. 26, 2973, abandoned, which is a continuation-in-part of Ser. No. 26,742, Apr. 8, 1970, abandoned.

[30] Foreign Application Priority Data

Apr. 10, 1969 [BE] Belgium .................................. 731359
Nov. 13, 1969 [BE] Belgium .................................. 741640
Mar. 31, 1970 [BE] Belgium .................................. 87126

[51] Int. Cl.$^2$ ...................... C07C 25/14; C07C 47/55; C07C 49/80; C07C 121/66
[52] U.S. Cl. ............................... 260/465 G; 562/459; 568/662; 568/655; 562/495; 568/774; 546/346; 260/326.8; 546/230; 546/232; 260/465 D; 546/235; 546/229; 260/465 F; 546/238; 546/239; 260/570.5 R; 546/240; 546/236; 260/570.8 R; 260/577; 260/590 R; 260/599; 260/607 AR; 260/609 E; 260/646; 260/649 R; 260/650 F; 260/651 R; 260/651 HA; 560/9; 560/83; 560/103; 560/254; 546/205; 546/330; 546/334; 546/335; 546/338; 546/342; 546/344; 546/339; 260/348.12; 260/348.49; 568/812
[58] Field of Search ....... 260/465 G, 290 HL, 590 R, 260/599, 618 D, 651 R, 649 R, 651 HA; 560/103

[56] References Cited

FOREIGN PATENT DOCUMENTS

714573 12/1941 Fed. Rep. of Germany.
960205 3/1957 Fed. Rep. of Germany.
1212098 3/1966 Fed. Rep. of Germany.
1097579 1/1968 United Kingdom.

OTHER PUBLICATIONS

Fieser et al., J. Am. Chem. Soc., vol. 60, pp. 1142–1144 (1938).
Muller, Angew. Chem., vol. 61, pp. 179–183 (1949).
Kozlov, J. General Chem., USSR, vol. 31, pp. 2059–2063 (1960).
Dombrovskii et al., Chem. Abst., vol. 51, 7337, 8038 (1957).
USSR patent 187,034, Chem. Abst., vol. 67, 73335 (1967).
Malinowski et al., Chem. Abst., vol. 49, 1034–1035 (1955).
Brunner et al., Chem. Abst., vol. 44, 1054g (1950).
Organic Reactions II, pp. 189–260 (1960).
Houben-Weyl "Methoden der Organischen Chemie" (1965), Part 10/3, pp. 25, 26, 28, 30, 31, 172, 173.
Koelsch, J. Am. Chem. Soc., vol. 65, pp. 57–58 (1943).

*Primary Examiner*—Dolph H. Torrence
*Attorney, Agent, or Firm*—Haseltine, Lake & Waters

[57] ABSTRACT

A process for arylating an olefinic compound by addition of an aryl group to a double bond of said olefinic compound consisting in diazotizing an arylamine in an aqueous acidic solution comprising a lower alkanoic acid to form a solution of an aryldiazonium salt and reacting said aryldiazonium salt solution with an olefinic compound in an organic solvent in the presence of a catalytically effective amount of a copper halide.

The amount of alkanoic acid is about 15 to 37% by volume of the total solvents used. The alkanoic acid is preferably acetic acid and the copper halide cuprous chloride.

12 Claims, No Drawings

PROCESS FOR THE ARYLATION OF OLEFINES

This application is a continuation of Ser. No.: 345,197 filed Mar. 26, 1973 and now abandoned which is a continuation-in-part application of Ser. No. 26,742 filed Apr. 8, 1970, now abandoned.

The present invention relates to a process for arylating an olefinic compound consisting in diazotizing an arylamine in the presence of an alkanoic acid to produce the corresponding aryldiazonium salt and reacting said aryldiazonium salt with an olefinic compound in an organic solvent in the presence of a catalytically effective amount of a copper halide.

More specifically it concerns a process for arylating an olefinic compound by addition of an aryl group to a double bond of said olefinic compound consisting in diazotizing an arylamine in an aqueous acidic solution comprising a lower alkanoic acid to form a solution of an aryldiazonium salt and reacting said aryldiazonium salt solution with an olefinic compound in an organic solvent in the presence of a catalytically effective amount of a copper halide.

The reaction of arylating unsaturated olefins by way of the corresponding aryldiazonium halides in the presence of a catalyst is known and described in the literature under the name of "*Meerwein's reaction*" (J. Prakt. Chem. 152 (1939) 237-266).

This reaction can be summarized as follows:
(a) Diazotization of an arylamine, and afterwards
(b) Reaction of the aryldiazonium salt obtained with an olefin in the presence of a catalyst.

With a few exceptions the yields provided by this known method are usually mediocre and even very low.

It is also known that to reduce the formation of by-products, inter alia those affected by Sandemeyer's reaction, the arylation reaction of interest has previously had to be performed at temperatures which are often very low, with the result that not only was the speed of the arylation reaction reduced and in some cases made nil but also that the reaction had to be performed very slowly; consequently, this method has given satisfactory results only with a very reduced number of arylamines and olefins.

The new process according to this invention helps to obviate the disavantages just mentioned and therefore forms a considerable technical advance as regards syntheses residing in fixing the variously substituted hydrocarbon chains to aromatic nuclei.

Some of the main advantages provided by the process according to the invention are as follows:

1. The yields of this olefin arylation reaction are improved considerably;
2. The arylation reaction is performed at optimum temperature and in a much shorter time than previously;
3. As compared with the conventional method much smaller quantities of copper, preferably cuprous, halide are required as catalyst;
4. The arylation reaction according to the invention may be used with a much larger number of arylamines, and
5. The arylation reaction can now be used with a wide range of olefins.

A main feature of the novel process is that the arylamines used are diazotized in the presence of an alkanoic acid to produce the corresponding aryldiazonium salts in a medium very advantageous for reacting such salts with the olefins, such reaction leading to the saturation of the reactive $>C=C<$ bond of the olefins by the addition of the aryl group and of the halogen atom.

The improvements and advantages provided by the process according to the invention arise from using an alkanoic acid as co-solvent, not only in diazotization of the arylamines but also in the reaction of the corresponding aryldiazonium salts with the olefins which are themselves dissolved, e.g. in acetone, the latter reaction being performed in the presence of a copper, preferably cuprous, halide as catalyst.

Acetic, formic, propionic, etc. acids are examples of alkanoic acids which may be used for the purposes of this invention, acetic acid being preferred.

An advantage which the process according to the invention has over conventional procedure is that the alkanoic acid replaces some of the considerable quantities of water and even ice conventionally used to diazotize the arylamines, and so the amounts of water can be reduced very considerably. Also, the presence of an alkanoic acid in the olefins arylation reaction makes it possible to work in a very advantageous organic medium, leading to arylated compounds being produced at considerably improved yields and with considerably reduced reaction times. Thanks to the process according to the invention, a very wide range of arylated compounds not previously described nor known have been synthesized in advantageous economic conditions.

It is known to cause diazonium salt to react with the olefinic compound in the presence of sodium acetate. Experiments show however that the use of an acetate in the reaction does not produce good results because an extremely high amount of residue by-product is formed.

It is known that sodium acetate is used as a buffer in order to maintain an optimum pH in the reaction medium. See:

C. F. Koelsh (J. Org. Chem. 65 (1943) 57 and

"*Arylation of Unsaturated Compounds by Diazonium Salts*" publisher: John Wiley and Sons, 1960, Editor-in-Chief Adams.

It must also be considered that:

A/ in the process in which sodium acetate is used:
- much water is present
- the arylation reaction begins at a pH which is at least 3
- the medium is an organic medium which is poor (much water)
- the percentage in salt (NaCl) is high.

B/ In the case of the invention:
- a relatively small quantity of water is used
- the arylation reaction may begin at a pH = 0 to 1
- the medium is more "organic" than in the case of acetate
- the percentage in salt is relatively small.

The combination of the feature at the basis of the invention is that with the use of alkanoic acid in cooperation with the preferred use of a small amount of cuprous halide it is possible to perform the olefin arylation reaction via the aryldiazonium halides at a lower temperature and faster than in the case of the known conventional method.

With the process according to the invention, therefore, it becomes possible to perform the olefin arylation reaction at optimum temperature, so that the formation of by-products, inter alia those affected by Sandmeyer's reaction, is greatly reduced.

The process according to the invention has the particular advantage of extending the scope of the present arylation reaction to a much wider range of arylamines and olefins than are accessible to the known conventional method.

This olefin arylation reaction can be represented for the purpose of this invention by the following diagram:

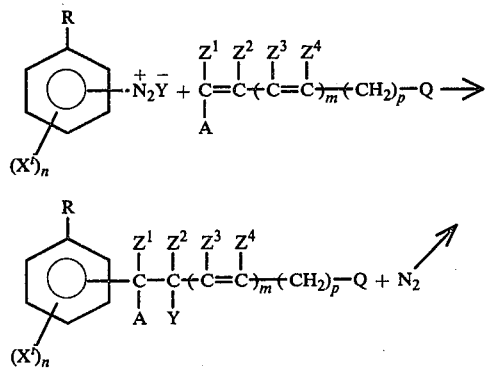

in which:

$Z^1$, $Z^2$, $Z^3$ and $Z^4$, which may or may not be similar, are selected from the following atoms or groups: hydrogen, halogen or lower alkyl radical;

A denotes either a hydrogen atom or a lower alkyl radical;

Q can denote an atom of hydrogen or a halogen or one of the following groups: cyano, nitro, hydroxy, methyl, trifluoromethyl, epoxyalkyl, alkoxy, alkenoxy, alkylsulfonyl, alkenylsulfonyl, alkylamino, alkenylamino, carbalkoxy, with the possibility of any alkyl or alkenyl chain, whether or not branched, being or not being substituted by one or more halogens or by a hydroxy or carboxy group; Q can also denote one of the aryl or aryloxy or aryloxycarbonyl groups in which the aryl radical may or may not have one or more substituents such as halogen, trifluoromethyl, alkyl, alkoxy, alkenyloxy, nitro or carboxy; or else Q can denote an acyl or acyloxy group or a cycloalkyl or cycloalkenyl radical or a heterocyclic group such as pyridyl, piperidyl, pyrrolidyl, morpholinyl etc; R can denote a hydrogen atom, a lower alkyl group, the trifluoromethyl radical, a hydroxy, a lower alkoxy or alkylthio or dialkylamino group or the phenyl or phenoxy or phenylthio radical in which the phenyl nucleus may or may not be substituted by at least one halogen and possibly by one of the following radicals:

—$CF_3$, —$NO_2$, —CN, —COOH or

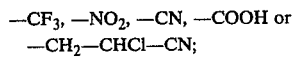

The radicals $X^i$, which may or may not be similar, are selected from the following atoms or groups: hydrogen, halogen, lower alkyl, nitro, cyano or carboxy; also, R and one of the radicals $X^i$ can be so combined as together to denote a single tri-atomic or tetra-atomic chain which may or may not be saturated and which is fixed by its end atoms to the benzene nucleus having the general formula hereinbefore given to form a bicyclic molecule of the naphthalenic or benzoheterocyclic kind;

Y denotes a halogen;

n is any of the whole numbers 1–4;

m is any of the whole numbers zero or 1, and p is any whole number having the value zero or 1 or 2.

As non-limitative examples of olefin derivatives suitable for the arylation reaction process according to the invention, there may be mentioned: Ethylene, vinyl chloride, 1,1-dichloroethene, 1,1,2-trichloroethene, allyl alcohol, allyl chloride, vinylacetonitrile, crotyl chloride, crotonic alcohol, crotonic aldehyde, crotonic nitrile, crotonic acid and esters, acrolein, methacrolein, 4-methylpent-3-ene-2-one, methyl vinyl ketone, styrene, 2-vinylpyridine, 4-vinylpyridine, 4-vinylcyclohex-1-one, N-vinyl-pyrrolid-2-one, methyl acrylate, methyl methacrylate, methyl-α-chloroacrylate, vinyl acetate, acrylonitrile, methacrylonitrile, α-chloroacrylonitrile, butadiene, isoprene, 2,3-dichlorobutadiene, butadiene monoxide, methallylalcohol, methallyl chloride, 3-chloro-1-butene, diallylether, allyloxypropanol, diallylamine, 2-methyl-3-butene-2-ol, allyl formate, glycidyl acrylate, glycidyl methacrylate, divinylsulfone, diallyl succinate, diallyl malonate, allyl acetate etc.

The olefin arylation reaction via aryldiazonium halides can be summed up as follows:

(a) Diazotization of an arylamine in a halohydric medium, and (b) Reaction of the resulting aryldiazonium salt with the olefin in the presence of a copper halide as catalyst and in an organic solvent, for instance, acetonic, medium.

According to this invention, the reaction of the aryldiazonium salt with the olefin in a catalyzed medium is performed, in the presence, besides acetone, of an alkanoic acid, preferably acetic acid, as co-solvent such that the amount of alkanoic acid is about 15 to 37% by volume of the total solvents used. So that working can be continuous starting from the arylamines, the same are diazotized in the presence of the same co-solvent - i.e., the alkanoic acid mentioned previously.

There are various possible forms of working. The alkanoic acid solution of the diazonium salt can be added to the olefin which is itself in solution, e.g. in acetone, whereafter the catalyst, preferably a cuprous halide, is added. Alternatively, the olefin acetone solution and the catalyst can be added simultaneously to the diazonium salt alkanoic acid solution. Alternatively, the diazonium salt solution and the catalyst can be added simultaneously to the acetone solution of olefin.

The temperature of the arylation reaction depends upon the nature of the olefin and is from 0° to 40° C., preferably from 0° to 25° C.

To show the advantage of using an alkanoic acid as co-solvent in the arylation reaction according to this invention, the results of various preparations of α-chloro-β-(3-chloro-tolyl)propionitrile, performed with and without the presence of an alkanoic acid, are listed by way of example in Table 1 hereinafter.

Except for the copper salt, the nature and quantities of reagents are identical in the various experiments. The reaction of 6-chlorotoluene-2-diazonium chloride with acrylonitrile was performed at the same temperature of 22° C. in every experiment.

Experiments I to VI are distinguished by the co-solvent being alkanoic acid. In Experiments VII and VIII the alkanoic acid was replaced by the same volume of water, and in experiment IX the alkanoic acid is replaced by the same volume of a sodium acetate solution.

In the latter case the final pH of the reaction medium is only 3.5.

Some writers recommend using sodium acetate in cyanoalkylation reactions of this kind so as to reduce the acidity of the medium. The results of experiment IX show that this reduction is acidity is a disadvantage which leads to the formation of a very considerable residue.

TABLE 1

| | Starting from 1 mob of arylamine and 1.5 mols of acrylonitrile. | | | | | |
|---|---|---|---|---|---|---|
| Experiment No. | Co-solvent or other | cyanoalkylation catalyst | Yield (*) | By-products A | B | C |
| I | formic acid | 10 g CaCl | 150 g | 18 g | 5 g | 7 g |
| II | formic acid | 25 g $CuCl_2 \cdot 2H_2O$ | 145 g | 14 g | 4 g | 7 g |
| III | acetic acid | 10 g CuCl | 169.2 g | 11.2 g | 6 g | 7 g |
| IV | acetic acid | 25 g $CuCl_2 \cdot 2H_2O$ | 160.6 g | 19.7 g | 7 g | 7.5 g |
| V | propionic acid | 10 g CuCl | 166 g | 13 g | 5 g | 6 g |
| VI | propionic acid | 25 g $CuCl_2 \cdot 2H_2O$ | 165 g | 7 g | 4 g | 7 g |
| VII | water | 10 g CuCl | 65 g | 22.5 g | 37.2 g | 20 g |
| VIII | water | 25 g | 115 g | 12 g | 21.4 g | 26 g |
| IX | water + acetate | 25 g $CuCl_2 2H_2O$ | 107.3 g | 10 g | 10 g | 43 g |

(*) : α-chloro-β-(3-chlor-o-tolyl)propionitrile
A : mono- and dichlorotoluene
B : chlorinated cresol
C : residue Table 1 clearly shows that using an alkanoic acid as co-solvent in accordance with the process provided by this invention considerably helps the cyanoalkylation reaction. There is a considerable increase in the yields of α-halogeno-β-arylpropionitriles, mainly as the result of a considerable decrease in the quantities of by-product found in the reaction (chlorinated aryls, phenol derivatives and resin residue).

Another advantage of this invention is that the improved yields of α-halogeno-β-arylpropionitriles are obtained when the use of alkanoic acid as co-solvent is combined, so far as the actual cyanoalkylation reaction is concerned, with the use as catalyst of cuprous chloride, CuCl. Also, considering the respective copper contents the quantities of cuprous chloride required are less than when cupric chloride, $CuCl_2.2H_2O$, is used; 10 g (0.1 mole) of CuCl per mole of arylamine are adequate, as compared with 25 g (0.15 mole) of $CuCl_2.2H_2O$.

The reaction time is another important factor. Using an alkanoic acid according to the invention considerably reduces the time of the reaction between the aryldiazonium salt and the acrylonitrile (or an α-substituted derivative thereof). This finding is apparent from Table 2 which gives a comparison of the times of this cyanoalkylation reaction in the presence and absence of acetic acid as co-solvent, the two kinds of catalyst previously mentioned having been used in every case.

TABLE 2

| Co-solvent | copper salt | reaction time |
|---|---|---|
| acetic acid | CuCl | 4 hours |
| acetic acid | $CuCl_2 . 2 H_2O$ | 4.25 h. |
| water | CuCl | 24 h. |
| water | $CuCl_2 . 2 H_2O$ | >10 h. |

One of the further advantages provided by this invention is that the process according to the invention provides at very reduced cost a whole range of intermediate products covering different spheres in the present-day chemical industry.

All the advantages of the process according to the invention and hereinbefore described are all the more clearly apparent in that it has been found possible to confirm them in the successful use of the process according to the invention with a wide and varied collection of olefins and arylamines, leading to the synthesis of many kinds of arylated derivatives which have previously been reachable only by the usual methods of organic chemistry.

The following examples explain this invention but do not limit its scope.

EXAMPLE 1:

a) 280 ml of acetic acid and 280 ml of concentrated (9 N) hydrochloric acid are introduced into a 2-liter reactor having an agitator, a thermometer and a dropping funnel. 141.5 g (1 mole) of 6-chloro-o-toluidine are added in drops with vigorous agitation. The reaction mixture is cooled to 0° C., whereafter 150 ml. of aqueous solution containing 75 g of sodium nitrite is introduced drop by drop over a period of 15 minutes, the temperature being maintained between 0° and +4° C., with vigorous agitation. The end of the dropping funnel must dip into the liquid. The mixture is allowed to react for a few minutes, whereafter the diazonium salt solution is filtered on a fritted glass filter.

b) 120 ml of acetone and 90 g of acrylonitrile (1.5 mole) are introduced into a 2-liter reactor having an agitator, a coolant and 2 dropping funnels. The diazonium salt solution is added over a period of from 10 to 15 minutes simultaneously with a solution of 10 g of freshly prepared cuprous chloride in hydrochloric acid. The reaction medium is agitated slowly, the temperature being maintained at 22° C. When the evolution of nitrogen has completely stopped, denoting the end of the reaction, the two layers which have formed are separated. The aqueous layer is extracted twice with 50 ml of $CCl_4$ which are added to the organic layer. To remove the chlorccresol formed, the organic layer is washed several times in a 2N NaOH solution. After washing with water and drying on $CaCl_2$ the mixture is distilled in vacuo. The top fraction consists of mono- and di-chlorotoluenes. The α-chloro-β-(3-chloro-o-tolyl)propionitrile distills between 115° and 125° C. at a pressure of 0.1 mm and is a slightly yellowish liquid having a density of 1.2541 at 25° C. Analysis shows the percentage of chlorine to be 32.98, as compared with the theoretical figure of 33.17%. 169.2 g of this product, corresponding to 79% of the theoretical yield, are obtained. 7 g of undistillable residue remain in the distillation flask.

EXAMPLE 2

138 g (1 mole) of m-nitro-aniline are slowly added in a 2-liter reactor to a mixture of 300 ml of concentrated HCl, 150 ml of water and 150 ml of acetic acid. The mixture is heated until the amine hydrochloride dissolves, whereafter the mixture is cooled to 0° C. with vigorous agitation. With the temperature remaining between 0° and 3° C., 70 g of $NaHO_2$ dissolved in 150 ml of $H_2O$ are added.. The m-nitro-benzene-diazonium chloride solution is added simultaneously with an aqueous solution of 25 g of $CuCl_2.2H_2O$ to a solution of 87 g of α-chloro-acrylonitrile in 150 ml of acetone. The temperature is kept at 30° C. Evolution of nitrogen ceases after about 6 hours. The α,α-dichloro-β-(3-nitrophenyl)propionitrile is extracted with benzene, washed in sodium hydroxide, then washed with water. After drying and removal of the solvent the product is distilled at low pressure. 215 g of α,α-dichloro-β-(3-nitrophenyl)propionitrile, corresponding to an 88% yield, are obtained, in the form of a slightly pinkish oil distilling at 140° C. at a pressure of 0.1 mm.

Analysis: % Cl calculated: 28.97 % Cl found: 29.00

EXAMPLE 3

162 g of 3,4-dichloroaniline are added to a mixture of 280 ml of concentrated HCl and 280 ml of formic acid. The mixture is heated until the amine hydrochloride dissolves. After cooling to 0° C., the mixture has slowly added to it 75 g of $NaNO_2$, dissolved in 150 ml of water, the temperature remaining between 0° and 3° C. The diazonium salt solution is filtered, then added simultaneously with an aqueous solution of $CuCl_2.2H_2O$ to a mixture of 120 ml of acetone and 100 g of methacrylonitrile. The temperature is maintained at 22° C. Upon completion of the reaction the two layers which have formed are separated, and the aqueous layer is extracted with 50 ml of $CCl_4$; the $CCl_4$ extract is added to the organic layer. After washing in diluted sodium hydroxide and then in water, the solution is dried on $CaCl_2$. The solvent is eliminated and the product distilled in vacuo at a pressure of 0.1 mm (B.P.$_{0.1}$: 135°–140° C.). 178 g, corresponding to a 71.6% yield, are obtained of α-chloro-β-methyl-β-(3,4-dichlorophenyl)propionitrile in the form of an oil which slowly solidifies.

Analysis: % of chlorine calculated: 42.85 % of chlorine found: 42.38

EXAMPLE 4

196.4 g of 2,4,6-trichloroaniline are added to a mixture of 660 ml of concentrated (9 N) HCl, 200 ml of water and 660 ml of acetic acid in a 3-liter reactor having and agitator, a thermometer and a dropping funnel. Heating is continued until the amine hydrochloride dissolves, whereafter the mixture is cooled to 0° C. with vigorous agitation. 150 ml of aqueous solution containing 75 g of sodium nitrite are then introduced drop by drop over a period of 15 minutes, the temperature remaining between 0° and 4° C., with vigorous agitation. The mixture is left to react for a few minutes, whereafter the diazonium salt solution is filtered on a fritted glass filter.

120 ml of acetone and 120 g of methyl α-chloroacrylate are introduced into a 3-liter reactor having an agitator, a coolant and two dropping funnels. The diazonium salt solution and a solution of 10 g of cuprous chloride in hydrochloric acid are added simultaneously over a period of 10 minutes. The reaction medium is agitated slowly, the temperature being maintained at from 12° to 15° C. Upon the complete cessation of evolution of nitrogen, denoting completion of the reaction, the two layers which have formed are separated. The aqueous layer is extracted twice with 50 ml of ether which are added to the organic layer. To remove the chlorophenol formed the organic layer is washed a number of times with a (2 N) NaOH solution. After washing in water, drying on $CaCl_2$ and evaporation of the solvent the product is distilled in vacuo at a pressure of 0.8 mm (B.P. 0.8 at 130°–135° C.). 235 g, corresponding to a 70% yield, of methyl α,α-dichloro-β-(2,4,6-trichlorophenyl)propionate are obtained in the form of an oil which solidifies slowly (M.P.: 56°–57° C.).

Analysis: % Cl found 51.5 % Cl calculated: 52.74

EXAMPLE 5

β-chloro-α(3-chlorophenyl)butyronitrile is prepared similarly. 127.4 g of 3-chloroaniline are diazotized in a mixture of 280 ml of concentrated (9 N) HCl and 280 ml of acetic acid, diazotization being performed by an addition of 75 g of $NaNO_2$ dissolved in 150 ml of water. After filtering the 3-chlorobenzenediazonium chloride solution is added, simultaneously with an aqueous solution of 25 g of $CuCl_2.2 H_2O$ to a mixture of 115 g of vinylacetonitrile and 120 ml of acetone. The mixture is agitated slowly, the temperature being maintained at 20° C. Upon cessation of the evolution of nitrogen, the β-chloro-γ-(3-chlorophenyl)butyronitrile is isolated in the same way as described in example 1.

145 g, corresponding to 68% yield, of a yellowish oil distilling between 120° and 130° C. at a pressure of 0.8 mm are obtained.

Analysis: % Cl found: 34 % Cl calculated: 33.13

EXAMPLE 6

Preparation of β,β,2,6-tetrachloroethylbenzene.

162 g. (1 mole) of 2,6-dichloroaniline are slowly added with agitation to a mixture of 280 ml of concentrated HCl and 280 ml of acetic acid in a 2-liter reactor. The mixture is heated until the amine hydrochloride dissolves, whereafter the mixture is cooled to 0° C. with vigorous agitation. With the temperature remaining between 0° and 3° C. 70 g of $NaNO_2$ dissolved in 150 ml of water are added. The resulting 2,6-dichlorobenzenediazoniumchloride solution is added simultaneously with a solution of 5 g of CuCl in 50 ml of HCl to a mixture of vinyl chloride and 500 ml of acetone. While the diazonium salt is being added the temperature is maintained between 0° and 5° C., then raised to 10° C., vinyl chloride being bubbled through for 1 hour. The evolution of nitrogen ceases after a reaction time of 3 hours.

The β,β,2,6-tetrachloroethylbenzene formed is extracted with ether and washed several times in a dilute NaOH solution and then washed in water. The solvent is removed and the product is distilled in vacuo at a pressure of 0.01 mm (B.P.$_{0.01}$ 106°–107° C.). 175 g, corresponding to a 72% yield, are obtained, in the form of an oil, of β,β,2,6-tetrachloroethylbenzene.

Analysis: % Cl found: 57.6 % Cl calculated: 58.19

EXAMPLE 7

2-chloro-3-(5-chloro-o-tolyl)propanol can be prepared similarly. 141 g of 4-chloro-o-toluidine are diazotized in a mixture of 280 ml of concentrated (9 N) HCl and 280 ml of acetic acid, diazotization being performed by the addition of 75 g of $NaNO_2$ dissolved in 150 ml of water. After filtration the 4-chlorotoluene-2-diazonium solution is added simultaneously with a solution of 5 g of CuCl in 50 ml of HCl to a mixture of 90 g of allyl alcohol and 120 ml of acetone. Slow agitation is applied and the temperature is maintained at from 30° to 32° C. When the evolution of nitrogen, ceases, the 2-chloro-3-(5-chloro-o-tolyl) propanol is isolated similarly as described in example 6. 104 g of a yellowish oil, corresponding to a 48% yield, are obtained, the oil distilling between 130° and 133° C. at a pressure of 0.01 mm.

Analysis: % Cl found 30.7 % Cl calculated: 31.5

EXAMPLE 8

Preparation of α-chloro-β-(2-chloro-5-trifluoromethylphenyl)propionaldehyde.

195.5 g (1 mole) of 2-chloro-5-trifluoromethylaniline are added to a mixture of 280 ml of concentrated HCl and 280 ml of acetic acid. After the mixture has been cooled to 0° C., 75 g of $NaNO_2$ dissolved in 150 ml of water are slowly added to the mixture, the temperature being maintained between 0° and 3° C. At the same temperature, a mixture of 5 g of CaO and 60 g of acrolein dissolved in 250 ml of acetone is then introduced. A solution of 1 g of CuCl in 20 ml of concentrated HCl is then added; the temperature is maintained between 5° and 10° C. The evolution of nitrogen ceases after a reaction time of 1 hour. The α-chloro-β-(2-chloro-5-trifluoromethyl-phenyl)propionaldehyde is extracted by ether and washed in water. After drying and removal of the solvent the product is distilled at a reduced pressure. 135 g, corresponding to a 50% yield, of a slightly yellowish oil distilling between 98° and 100° C. at a pressure of 0.5 mm are obtained.

Analysis: % Cl found 25.2 % Cl calculated: 26.05

EXAMPLE 9

Preparation of 1-(2,3,4-trichlorophenyl)-2-chlorobutan-3-one.

196.5 g of 2,3,4-trichloroaniline are added to a mixture of 500 ml of concentrated HCl and 500 ml of acetic acid. The mixture is heated until the amine hydrochloride dissolves. The mixture is then cooled to 0° C., and 75 g of $NaNO_2$ dissolved in 150 ml of water are slowly added, the temperature being maintained between 0° and 3° C. The diazonium salt solution is filtered, then introduced simultaneously with a solution of 0.5 g CuCl in 30 ml of HCl into a mixture of 180 ml of acetone +105 g of methyl vinyl ketone and 3 g of CaO. The evolution of nitrogen ceases after a reaction time of about 30 minutes at 30° C. The 1-(2,3,4-trichlorophenyl)-2-chlorobutane-3-one formed is extracted in ether, washed a number of times in dilute NaOH, then washed in water. After drying on $CaCl_2$ the solvent is removed and the product is distilled in vacuo (B.P.$_{0.05}$: 155°–157° C.). 138 g, corresponding to a 48% yield, of 1-(2,3,4-trichlorophenyl)-2-chlorobutan-3-one in the form of an oil which slowly solidifies (M.P.: 62°–63° C.) are obtained.

Analysis: % Cl found 48.95 % Cl calculated: 47.35

EXAMPLE 10

Preparation 1-chloro-3-methyl-4-(6-chloro-o-tolyl)but-2-ene.

141.5 g of 3-chloro-o-toluidine are introduced slowly and with agitation into a mixture of 280 ml of acetic acid and 280 ml of concentrated HCl in a 3-liter reactor having an agitator, a thermometer and a dropping funnel. 150 ml of an aqueous solution containing 74 g of sodium nitrite are added drop by drop over a period of 15 minutes; the temperature is maintained between 0° and 5° C. The mixture is left to react for a few minutes after the addition of the reagents. A mixture of 240 ml of acetone and 150 g of isoprene is added to the resulting diazonium salt solution over a period of 45 minutes, the temperature being maintained at 0° C. Simultaneously as the isoprene and acetone are added, 8 g of CuCl dissolved in 80 ml of concentrated HCl are added to the diazoic solution. The reaction medium is maintained at 0° C. for 3 hours and then at from 15°–20° C. for 4 hours. When the evolution of nitrogen has completely ceased, denoting the end of the reaction, the two layers formed are separated. The aqueous layer is extracted twice in 100 ml of ether and the ethereal extract is added to the organic layer. To eliminate the chlorocresol formed in the reaction the organic layer is washed a number of times in a (2 N) NaOH solution. The product is then washed in water and dried on $CaCl_2$; the solvent is evaporated and the residue distilled at reduced pressure. 160 g, representing a 72% yield, of 1-chloro-3-methyl-4-(6-chloro-o-tolyl)butene-2 in the form of an oil distilling between 112° and 114° C. at a pressure of 0.1 mm Hg are obtained.

Analysis: % Cl found: 29.98 % Cl calculated: 31.00

EXAMPLE 11

Preparation of 1,2,3-trichloro-4-(2,4,5-trichlorophenyl)but-2-ene.

196.5 g of 2,4,5-trichloroaniline are added to a mixture of 500 ml of concentrated HCl and 500 ml of acetic acid. Heating continues until the amine hydrochloride formed is dissolved. After the mixture has cooled to 0° C., 75 g of sodium nitrite dissolved in 150 ml of water are slowly introduced, the temperature being maintained between 0° and 3° C. After filtering of the diazonium salt solution, the same is introduced into a mixture of 240 ml of acetone +120 ml of 2,3-dichlorobutadiene +1 g of hydroquinone, whereafter a solution of 7.5 g of CuCl dissolved in 70 ml of concentrated HCl is added at a temperature of from 10°–12° C. over a period of from 3 to 4 hours. When the evolution of nitrogen ceases, the 1,2,3-trichloro-4-(2,4,5-trichlorophenyl)butene-2 is extracted in ether; the ethereal extract is washed a number of times in a dilute NaOH solution, then washed in water. After drying on $CaCl_2$ and elimination of the solvent the product is distilled at a reduced pressure. 221 g, corresponding to a 65% yield, of a yellowish oil distilling between 152° and 156° C. at a pressure of 0.2 mm Hg are obtained.

Analysis: % Cl found 62.3 % Cl calculated: 62.83

EXAMPLE 12

Preparation of 1-(2,6-dichlorophenyl)-4-chlorobutene-2

162 g of 2,6-dichloroaniline are diazotized in a mixture of 300 ml of concentrated (9 N) HCl and 300 ml of acetic acid, diazotization being performed by an addition of 75 g of $NaNO_2$ dissolved in 180 ml of water. This diazoic solution is added, simultaneously with a solution of 6 g of CuCl in 50 ml of concentrated HCl, to a mixture of 150 ml of butadiene and 1.2 liters of acetone, at a temperature of 0° C. and over a period of 30 minutes. After the addition of the reagents the reaction medium is left at 0° C. for 2 hours, then left to react at from 10°–12° C. for 10 hours. The 1-(2,6-dichlorophenyl)-4-chlorbutene-2 formed is extracted in ether, washed in a dilute NaOH solution a number of times, then washed in water. After evaporation of the solvent the product is distilled at reduced pressure in the presence of hydroquinone traces. 203 g, corresponding to an 87% yield, of an oil distilling between 116° and 118° C. at a pressure of 0.5 mm Hg are obtained.

Analysis: % Cl found: 44.50 % Cl calculated: 45.22

EXAMPLE 13

Preparation of 3,5,6,$\beta$,$\beta$,$\beta$-hexachloro-2-methylethylbenzene.

210 g (1 mole) of 3,4,6-trichloro-o-toluidine are diazotized in a mixture of 450 ml of acetic acid, 350 ml of (9 N) HCl and 100 ml of water, diazotization being performed by the addition of 75 g of NaNO$_2$ dissolved in 150 ml of water. After filtering the 3,4,6-trichloro-toluene-2-diazonium solution is added to a mixture of 150 ml of vinylidene chloride and 300 ml of acetone. While the mixture is agitated slowly and the temperature maintained at from 10° to 12° C., a solution of 6 g of CuCl in 70 ml of concentrated HCl is added over a period of from 3 to 4 hours. When the evolution of nitrogen ceases, the 3,5,6,$\beta$,$\beta$,$\beta$-hexachloro-2-methyl-ethylbenzene is isolated by ether extraction. The ethereal extract is processed as in example 12; 210 g, corresponding to a 63% yield, of an oil distilling between 122° and 125° C. at a pressure of 0.05 mm Hg are obtained.

Analysis: % Cl found: 65.4 % Cl calculated: 66.35

EXAMPLE 14

Preparation of 2-chloro-3-(2,5-dichlorophenyl)propyl acetate.

162 g of 2,5-dichloroaniline are diazotized in a mixture of 300 ml of concentrated (9 N) HCl and 300 ml of acetic acid, the diazotization being performed by the addition of 74 g of NaNO$_2$ dissolved in 150 ml of water, the temperature being maintained at 0° C. The 2,5-dichlorobenzenediazonium solution is filtered, then added to a mixture of 140 g of allyl acetate and 210 ml of acetone. 8 g of CuCl in 80 ml of concentrated HCl are then introduced at a temperature of from 17° to 20° C. over a period of 4 hours. The mixture is left to react for about 4 hours until all evolution of nitrogen has ceased. The 2-chloro-3-(2,5-dichlorophenyl)propyl acetate is isolated similarly to the products in the previous examples. 168 g, corresponding to a 55% yield, of an oil distilling between 136° and 138° at a pressure of 0.1 mm Hg are obtained.

Analysis: % Cl found: 36.9 % Cl calculated: 37.8

EXAMPLE 15

Preparation of $\alpha$-chloro-$\alpha$-methyl-$\beta$-(2,3-dichlorophenyl)propionaldehyde.

2,3-dichloroaniline hydrochloride is prepared by 162 g of dichloroaniline being added slowly and with vigorous agitation to a mixture of 280 ml of acetic acid and 280 ml of concentrated (9 N) HCl, diazotization being effected by the addition of 75 g of NaNO$_2$ dissolved in 150 ml of water, the temperature being maintained between 0° and 5° C. A mixture of 5 g of CaO and 60 ml of methacrolein (dissolved in 120 ml of acetone) and a solution of 6 g of CuCl dissolved in 60 ml of HCl are introduced simultaneously into the filtered diazonium salt solution over a period of 30 minutes. After the addition of the reagents the mixture is left to react at from 0° to 5° C. for 2 hours, then at from 10°–12° C. for 10 hours. The $\alpha$-chloro-$\alpha$-methyl-$\beta$-(2,3-dichlorophenyl)propionaldehyde is isolated similarly to the products in the previous examples. 206 g, corresponding to an 80% yield, of an oil distilling between 118° and 120° C. at a pressure of 0.01 mm Hg are obtained.

Analysis: % Cl found: 41.68 % Cl calculated: 42.74

EXAMPLE 16

Preparation of $\alpha$-chloro-$\beta$-(3-chloro-o-tolyl)2,3-epoxypropyl propionate.

141.5 g of 6-chloro-o-toluidine are slowly added with agitation to a mixture of 200 ml of concentrated HCl and 2.0 ml of acetic acid in a 3-liter reactor. The hydrochloride solution thus formed is cooled to 0° C., and 150 ml of an aqueous solution containing 74 g of NaNO$_2$ are added drop by drop over a period of 15 minutes. After filtering the 6-chlorotoluene-2-diazonium chloride solution is added to a mixture of 170 ml of glycidyl acrylate and 240 ml of acetone; whereafter a solution of 6 g of CuCl in 60 ml of HCl is added at a temperature of 25° C. over a period of 2 hours. The evolution of nitrogen ceases completely after 2 hours reaction time at 25° C. The $\alpha$-chloro-$\beta$-(3-chloro-o-tolyl)propionate of 2,3-epoxypropyl is extracted in ether and the ethereal extract is washed in water. After drying on CaCl$_2$ and removal of the solvent the residue is distilled at low pressure. 200 g, corresponding to a 70% yield, of an oil distilling between 195° and 200° C. at 0.1 mm Hg are obtained.

Analysis: % Cl found: 28 % Cl calculated: 27

EXAMPLES 17 to 139

(17) $\alpha$-bromo-$\beta$-(3-chloro-o-tolyl)propionitrile (b.p.$_{0.02}$: 130°–140° C.); yield: 56.2%; % hal.found: 45.9. % hal.calculated: 44.68.

(18) $\alpha$-chloro-$\beta$-(2,6-dichloro-4-nitrophenyl)propionitrile (m.p. 90°–92° C.); yield: 32%; % Cl found: 38.8. % Cl calculated: 38.1.

(19) $\alpha$-chloro-$\beta$-[4-(2,4-dichlorophenoxy)phenyl]propionitrile oily product; yield: 53%; % Cl found: 32.18. % Cl calculated: 32.62.

(20) $\alpha$-chloro-$\beta$-(3,5-dichloro-4-hydroxyphenyl)propionitrile (m.p. 75° C.), yield: 55%; % Cl found: 42.2. % Cl calculated: 42.51.

(21) $\alpha$-chloro-$\beta$-(2-iodophenyl)propionitrile (b.p.$_{0.1}$.106°–15° C.); yield: 47.2%; % N found: 4.6. % N calculated: 4.8.

(22) $\alpha$-chloro-$\beta$-(4-iodophenyl)propionitrile (b.p.$_{0.01}$.130°–5° C.); yield: 70%; % N found: 4.3. % N calculated: 4.8.

(23) $\alpha,\alpha$-dichloro-$\beta$-(4-iodophenyl)propionitrile (m.p. 50°–1°) (b.p.$_{0.01}$.140°–2°); yield 60%; % N found: 4.29. % N calculated: 4.15.

(24) $\alpha$-chloro-$\beta$-(2-fluorophenyl)propionitrile (m.p. 44°–5°) (b.p.$_{0.1}$.95°–100°); yield: 82.7%; % Cl found: 20.3. % Cl calculated: 19.34.

(25) $\alpha,\alpha$-dichloro-$\beta$-(2-fluorophenyl)propionitrile (b.p.$_{0.01}$. 74°–80°); yield: 79.2%; % Cl found: 31.4. % Cl calculated: 32.8.

(26) α-chloro-α-methyl-β-(2-fluorophenyl)propionitrile (b.p.$_1$. 76°–8°); yield: 76.4%; % Cl found: 18.5. % Cl calculated: 18.15.

(27) α,α-dichloro-β-(4-fluorophenyl)propionitrile (b.p.$_{0.1}$.80°–5°); yield: 77.9%; % Cl found: 32.2. % Cl calculated: 32.84.

(28) α-chloro-α-methyl-β-(4-fluorophenyl)propionitrile (b.p.$_{0.5}$.82°–6°); yield: 81%; % Cl found: 19.7. % Cl calculated: 18.15.

(29) α-chloro-β-(4-fluorophenyl)propionitrile (b.p.$_{0.01}$.90°–2°); yield: 72%; % Cl found: 19.2. % Cl calculated: 19.34.

(30) α-chloro-β-(3-trifluoromethyl-phenyl)propionitrile (b.p.$_{0.1}$.86°–92°); yield: 70.4%; % Cl found: 14.9. % Cl calculated: 15.2.

(31) α-chloro-β-(2-chloro-5-trifluoromethyl-phenyl)-propionitrile (b.p.$_{0.8}$.110°–2°); yield: 64%; % Cl found: 25.9. % Cl calculated: 26.5.

(32) α,α-dichloro-β-(2-chloro-5-trifluoromethyl-phenyl)propionitrile (b.p.$_{0.01}$.92°–4°); yield: 60%; % Cl found: 34.04. % Cl calculated: 35.2.

(33) α-chloro-β-(2-methoxy-4-chlorophenyl)propionitrile (b.p.$_{0.3}$.136°–40°); yield: 58%; % Cl found: 31.1. % Cl calculated: 30.87.

(34) α,α-dichloro-β-(2-methoxy-4-chlorophenyl)propionitrile (b.p.$_{0.01}$.128°–30°); yield: 62 %; % Cl found: 39.5. (m.p. 30°) % Cl calculated: 40.2.

(35) α-chloro-α-methyl-β-(2-methoxy-4-chlorophenyl)-propionitrile (m.p. 59°–60°); yield 59%; % Cl found: 29.8 (b.p.$_{0.01}$.128°–30°) % Cl calculated: 29.09

(36) α-chloro-β-(2,3,4,5-tetrachlorophenyl)propionitrile (m.p. 46°–7°); yield: 53%; % Cl found: 58.78. % Cl calculated: 58.48.

(37) α-chloro-β-(3-fluoro-p-tolyl)propionitrile (b.p.$_{0.01}$.110°–20°); yield: 71%; % N found: 7.25. % N calculated: 7.1.

(38) α-chloro-β-(2-iodo-4-chlorophenyl)propionitrile (b.p.$_{0.01}$.145°–55°); yield: 65%; % N found: 3.43. (m.p. 36°–7°) % N calculated: 3.45.

(39) α-chloro-β-(2,6-dichlorophenyl)propionitrile (m.p. 47°); yield: 67%; % Cl found: 42.65. % Cl calculated: 45.4.

(40) α-chloro-β-(2,4,6-trichlorophenyl)propionitrile (m.p. 40°–2°); yield: 62%; % Cl found: 52.8. % Cl calculated: 52.78.

(41) α-chloro-β-(2,4,5-trichlorophenyl)propionitrile (m.p. 52°–4°); yield: 65%; % Cl found: 53.7. % Cl calculated: 52.78.

(42) α-chloro-β-(2-chloro-4-nitrophenyl)propionitrile (oily product); yield 59%; % Cl found: 28.2. % Cl calculated: 27.72.

(43) α-chloro-β-(5,8-dichloro-1-naphthyl)propionitrile (m.p. 27°–30°); yield: 48%; % Cl found: 36.7. % Cl calculated: 37.41.

(44) α-chloro-β-(3-carboxy-4-chlorophenyl)propionitrile (m.p. 159°); yield: 56%; % N found: 5.8. % N calculated: 5.79.

(45) α,α'-dichloro-β,β'-(3,3'-dichloro-4,4'-biphenylene)di-propionitrile (m.p. 106°); % N found: 7.06. % Cl found: 33.5. % N calculated: 7.03. % Cl calculated: 35.4. yield: 50%

(46) α-chloro-β-(4-p-chlorophenoxy-phenyl)propionitrile (oily product); yield: 70%; % Cl found: 24.4. % Cl calculated: 24.31.

(47) α-chloro-β-[4-(2,4,5-trichlorophenylthio)phenyl]-propionitrile (viscous product) % S found: 8.6. yield: 45% % S calculated: 8.48.

(48) α,α-dichloro-β-(2,6-dichlorophenyl)propionitrile (m.p. 65°); yield: 68%; % Cl found: 52.3. % Cl calculated: 52.8.

(49) α-chloro-α-methyl-β-(3-chloro-o-tolyl)propionitrile (b.p.$_{0.01}$.120°–30°); % Cl found: 31. yield: 72% % Cl calculated: 31.14.

(50) α-chloro-β-(1-naphthyl)propionitrile (b.p.$_{0.1}$.160°–5°); % Cl found: 15.62. yield: 50% % Cl calculated: 16.47.

(51) α,α-dichloro-β-(1-naphthyl)propionitrile (b.p.$_{0.01}$.120°–30°) (m.p. 37°); yield: 41%

(52) α-chloro-β-(2-trifluoromethylphenyl)propionitrile (b.p.$_{0.01}$.78°–80°); yield: 82%.

(53) α,α-dichloro-β-(2-trifluoromethylphenyl)propionitrile (b.p.$_{0.01}$.80°–82°); yield: 80%.

(54) α-chloro-β-(4-dimethylaminophenyl)propionitrile (b.p.$_{0.01}$.130°–5°); yield: 49%.

(55) α-chloro-α-methyl-β-(2,6-dichloro-4-nitrophenyl)-propionitrile (m.p. 60°–1°); yield: 35%

(56) α,α-dichloro-β-(2,6-dichloro-4-nitrophenyl)propionitrile (m.p. 95°–97°); yield: 37%

(57) methyl α-chloro-β-(2,4,6-trichlorophenyl)propionate (b.p.$_{0.7}$.125°–130° C.); yield: 75%; % Cl found: 47.02. % Cl calculated: 47.02.

(58) methyl α-chloro-β-(2,6-chloro-4-nitrophenyl)propionate (b.p.$_{0.2}$.132°–135° C.); yield: 50%; % Cl found: 34.15. % Cl calculated: 34.08.

(59) methyl α-chloro-α-methyl-β-(2,4,5.-trichlorophenyl)propionate (b.p.$_{0.1}$.118°–120° C.); yield: 70%; % Cl found: 44.8. % Cl calculated: 44.93.

(60) methyl α-chloro-α-methyl-β-(4-cyanophenyl)propionate (b.p.$_{0.1}$.145°–147° C.); (m.p. 58°–60°); % Cl found: 14.98. yield: 82% % Cl calculated: 14.8.

(61) methyl α-chloro-α-methyl-β-(4-methylthiophenyl)propionate (b.p.$_{0.1}$.118°–120°); yield: 82%; % Cl found: 12.38. % Cl calculated: 12.43.

(62) methyl α-chloro-α-methyl-β-(4-chloro-o-tolyl)propionate (b.p.$_{0.01}$.105°–108°); yield: 70%; Cl found: 26.7. % Cl calculated: 27.2.

(63) methyl α,α-dichloro-β-(4-chlorophenyl)propionate (b.p.$_1$.118°–120°); yield: 75%; % Cl found: 39.2. % Cl calculated: 39.81.

(64) methyl α,α-dichloro-β-(3-chloro-o-tolyl)propionate (b.p.$_2$.130°–133°); yield: 70%; % Cl found: 37.60. % Cl calculated: 37.83.

(65) 2,2-dichloro-1-(2-fluorophenyl)ethane (b.p.$_{0.01}$.68°–70°); yield: 60%; % Cl found: 35.6. % Cl calculated: 36.78.

(66) 2,2,2-trichloro-1-(2,4.-dichlorophenyl)ethane (b.p.$_{0.7}$.140°–145°); (m.p. 66°); % Cl found: 62.4. yield: 65% % Cl calculated: 63.7.

(67) β-chloro-γ-(3-chlorophenyl)butyronitrile (b.p.$_{0.8}$.120°–130°); yield: 68%; % Cl found: 34. % Cl calculated: 33.13.

(68) β-chloro-γ-(3,4-dichlorophenyl)butyronitrile (b.p.$_{0.6}$.145°–150°); (m.p. 59°); % Cl found: 44. yield: 55% % Cl calculated: 42.85.

(69) β-chloro-γ-(3-chloro-o-tolyl)butyronitrile (b.p.$_1$.130°–135°); yield: 65%; % Cl found: 31.8. % Cl calculated: 31.14.

(70) 1,2.-dichloro-3-(2,4,6.-trichlorophenyl)propane (b.p.$_{0.4}$.128°–132°); (m.p. 45°–46°); % Cl found: 60.6. yield: 55% % Cl claculated: 60.68.

(71) 1,2-dichloro-3-(2,4,5-trichlorophenyl)propane (b.p.$_{0.4}$.135°–140°); (m.p. 42°–44°); % Cl found: 60.60. yield: 60% % Cl calculated: 60.68.

(72) 2-chloro-3-(4-chlorophenyl)propanol (b.p.$_{0.1}$ 125°–130°); yield: 60%; % Cl found: 34.17. % Cl calculated: 34.63.

(73) 2-chloro-3-(3-chloro-o-tolyl)propanol (b.p.$_1$.120°–123°); yield: 55%; % Cl found: 32.05. % Cl calculated: 32.42.

(74) 2,3-dichloro-4-(2-fluorophenyl)n-butane (b.p. 114°–116°); yield: 40%; % Cl found: 31.3. % Cl calculated: 32.12.

(75) 1,2-dichloro-3-(4-chlorophenyl)n-butane (b.p.$_{0.1}$.100°–114°); yield: 20%; % Cl found: 44.10. % Cl calculated: 44.84.

(76) α-chloro-β-(3-chloro-o-tolyl)propionaldehyde (b.p.$_{0.1}$.125°–130°); yield: 72%; % Cl found: 32.12. % Cl calculated: 32.72.

(77) α-chloro-β-(3-chlorophenyl)propionaldehyde (b.p.$_4$.115°–120°); yield: 63%; % Cl found: 33.12 % Cl calculated: 34.97

(78) α-chloro-β-(3-chloro-o-tolyl)n-butyraldehyde (b.p.$_{0.1}$.125°–130°); yield: 40%; % Cl found: 30 % Cl calculated: 30.74

(79) α-chloro-β-(2-fluorophenyl)n-butyronitrile (b.p.$_1$.94°–96°); yield: 35%; % Cl found: 17.3 % Cl calculated: 17.97

(80) α-chloro-β-(2,4-dichlorophenyl)n-butyronitrile (b.p.$_{0.1}$.132°–137°); yield: 40%; % Cl found: 40.08 % Cl calculated: 40.65

(81) 3-chloro-4-(2-chlorophenyl)n-butan-2-one (b.p.$_{0.1}$.104°–106°); yield: 75%; % Cl found: 31.7 % Cl calculated: 32.72

(82) 3-chloro-4-(4-nitrophenyl)n-butan-2-one (m.p. 78°–80°); yield: 70%; % Cl found: 15.56 % Cl calculated: 15.6

(83) 3-chloro-4-methyl-4-(2-chlorophenyl)pentan-3-one (b.p.$_{0.1}$.118°–120°); yield: 29%; % Cl found: 28.16 % Cl calculated: 28.98

(84) 3,β-dichloro-β-(2-oxo-pyrrolidino)ethylbenzene (m.p. 35°–38°); yield: 20%; % Cl found: 28.1 % Cl calculated: 27.5

(85) 3,4,β-trichloro-β-(2-oxo-pyrrolidino)ethylbenzene (m.p. 40°–42°); yield: 25%; % Cl found: 38.1 % Cl calculated: 36.41

(86) 2,β-dichloro-β-(4-pyridyl)ethylbenzene oily product; yield: 40%; % Cl found: 27.29 % Cl calculated: 28.17

(87) 3,β-dichloro-β-(2-pyridyl)ethylbenzene oily product: yield: 45%; % Cl found: 27.90. % Cl calculated: 28.17.

(88) 3,β-dichloro-2-methyl-β-(2-pyridyl)ethylbenzene oily product: yield: 45%; % Cl found: 26.18. % Cl calculated: 26.68.

(89) 1-chloro-1-(cyclohexen-4-yl)-2-(2-chlorophenyl)ethane (b.p.$_{0.1}$.135°–40°); yield: 35%: % Cl found: 28. % Cl calculated: 27.84.

(90) 1-chloro-2-(3-chloro-o-tolyl)ethyl acetate (b.p.$_{0.01}$.140°–3°)

(91) 1-chloro-2-(2-chloro-5-trifluoromethyl-phenyl)ethyl acetate (b.p.$_{0.1}$.100°–5°)

(92) β-chloro-γ-(4-chloro-o-tolyl)butyronitrile (b.p.$_{0.01}$.142°–144° C.); yield: 45%; % Cl found: 30.6. % Cl calculated: 31.4.

(93) α-chloro-β-(4-chloro-o-tolyl)propionaldehyde (b.p.$_{0.01}$.117°–120° C.); yield: 75%

(94) 2-chloro-3-(4-chloro-2-tolyl)propanol (b.p.$_{0.01}$.130°–132° C.); yield: 50% % Cl calculated: 31.5. % Cl found: 29.4.

(95) 1,2-dichloro-3-(4-chloro-o-tolyl)propane (b.p.0.01.110°–112° C.); yield: 30% % Cl calculated: 44.84. % Cl found: 43.1.

(96) 2-chloro-3-(3-chlorophenyl)propyl acetate (b.p.$_{0.01}$.123°–125° C.); yield: 35% % Cl calculated: 28.74. % Cl found: 28.82.

(97) α-chloro-β-(2,6-dichlorophenyl)propionaldehyde (b.p.0.01.120°–122° C.); yield: 40% % Cl calculated: 42.3. % Cl found: 40.4.

(98) α-chloro-β-(2,3,4-trichlorophenyl)propionaldehyde (b.p.$_{0.5}$: 160° C.); yield: 35%

(99) 1-(2,6-dichlorophenyl)-2-chlorobutan-3-one (b.p.$_{0.05}$.118°–122° C.); yield: 76% % Cl calculated: 42.34. % Cl found: 40.8.

(100) 1-(6-chloro-3-trifluoromethylphenyl)-2-chlorobutan-3-one (b.p.0.05.108°–120° C.); yield: 50%

(101) α,α-dichloro-β-(4-chloro-2-nitrophenyl)propionitrile (b.p.$_{0.01}$.140°–142° C.); yield: 75%; % Cl calculated: 38.10. % Cl found: 38.20.

(102) α-chloro-β-(4-cyanophenyl)propionitrile (b.p.$_{0.01}$.160°–162° C.); (m.p.: 74°–75° C.); % Cl calculated: 18.63. yield: 88%; % Cl found: 18.74.

(103) α-chloro-β-(4-methylthio-phenyl)propionitrile (m.p. 58°–60° C.); yield: 80%; % Cl calculated: 16.73. % Cl found: 17.

(104) 1-chloro-1-phenyl-2-(3-chloro-o-tolyl)ethane (b.p.$_{0.01}$.140°–143° C.); yield: 60%; % Cl calculated: 26.79. % Cl found: 26.5.

(105) β,β,β,2,6-pentachloroethylbenzene (b.p.$_{0.01}$.110°–112° C.); yield: 63%; % Cl calculated: 63.73. % Cl found: 62.74.

(106) β,β,2,3,4-pentachloroethylbenzene (b.p.$_{0.01}$.132°–134° C.); yield: 50%; % Cl calculated: 68.05. (m.p. 45°–6° C.) % Cl found: 66.

(107) 1-chloro-3-methyl-4-(2,6-dichlorophenyl)butene-2 (b.p.$_{0.01}$.130°–132° C.); yield: 60%; % Cl found: 42. % Cl calculated: 41.98.

(108) 1-chloro-3-methyl-4-(2-chlorophenyl)butene-2 (b.p.$_{0.01}$.94°–96° C.); yield: 66%; % Cl found: 31.55. % Cl calculated: 30.48.

(109) 1-chloro-3-methyl-4-(3-chloro-o-tolyl)butene-2 (b.p.$_{0.1}$.124°–126° C.); yield: 65%; % Cl found: 31. % Cl calculated: 29.9.

(110) 2-chloro-3-(3-chloro-o-tolyl)propyl formate (b.p.$_{0.1}$.122°–124° C.); yield: 55%; % Cl found: 26.60. decomposition % Cl calculated: 27.62.

(111) 2-chloro-3-(3,4-dichlorophenyl)propyl acetate (b.p.$_{0.01}$.148°–150° C.); yield: 55%; % Cl found: 36.60. % Cl calculated: 37.83.

(112) 1,2,3-trichloro-4-(2-chlorophenyl)butene-2 (b.p.$_{0.2}$.152°–156° C.); yield: 65%; % Cl found: 62.30. % Cl calculated: 62.83.

(113) 1,2-epoxy-3-chloro-4-(2-chlorophenyl)butane (b.p.$_{0.05}$.142°–145° C.); yield: 50%; % Cl found: 33.4. % Cl calculated: 32.71.

(114) 1-allyloxy-2-chloro-3-(3,4-dichlorophenyl)propane (b.p.$_{0.2}$.160°–165° C.); yield: 20%; % Cl found: 37.2. % Cl calculated: 38.1.

(115) 1-allyloxy-2-chloro-3-(2,5-dichlorophenyl)propane (b.p.$_{0.1}$.150°–153° C.); yield: 25%; % Cl found: 37.4. % Cl calculated: 38.1.

(116) 3-[2-chloro-3-(3-chloro-o-tolyl)propoxy]propanol (b.p.$_{0.01}$.144°–148° C.); yield: 25%; % Cl found: 24.95. % Cl calculated: 25.6.

(117) 1-allylamino-2-chloro-3-(2,6-dichlorophenyl)propane (not distillable oil); yield: 20%; % Cl found: 40.3. % Cl calculated: 38.6.

(118) β,β,β,2,4,5-hexachlorethylbenzene (b.p.$_{0.01}$.135°–140° C.); yield: 60%; % Cl found: 67.0. % Cl calculated: 68.05.

(119) 2-methyl-β,β,β,3-tetrachloro-ethylbenzene (b.p.$_{0.01}$.96°–100° C.); yield: 68%; % Cl found: 55.24. % Cl calculated: 55.04.

(120) 2-methyl-β,β,β,5-tetrachloro-ethylbenzene (b.p.$_{0.01}$.94°–96° C.); yield: 66%; % Cl found: 54.21. % Cl calculated: 55.04.

(121) 2-methyl-β,β,β,6-tetrachloro-ethylbenzene (b.p.$_{0.05}$.101°–103° C.); yield: 66%; % Cl found: 54.0. % Cl calculated: 55.04.

(122) 2-methyl-β,β,β,3,5-pentachloro-ethylbenzene (b.p.$_{0.01}$.112°–114° C.); yield: 68%; % Cl found: 61.0. % Cl calculated: 62.83.

(123) 3-methyl-β,β,β,2,6-pentachloro-ethylbenzene (b.p.$_{0.1}$.120°–123° C.); yield: 70%; % Cl found: 62.0. % Cl calculated: 62.83.

(124) 3-trifluoromethyl-β,β,β-trichloro-ethylbenzene (b.p.$_{0.05}$.68°–70° C.); yield: 70%; % Cl found: 37.12. % Cl calculated: 38.38.

(125) 4-nitro-β,β,β,2-tetrachloro-ethylbenzene (b.p.$_{0.1}$.144°–148° C.); yield: 50%: % Cl found: 48.50. (m.p.: 37° C.) % Cl calculated: 49.13.

(126) 1-chloro-4-(3,4-dichlorophenyl)butene-2 (b.p.$_{0.1}$.118°–120° C.); yield: 91%; % Cl calculated: 45.22

(127) 1-chloro-4-(3-chloro-o-tolyl)butene-2 (b.p.$_{0.5}$.120°–122° C.); yield: 80%; % Cl found: 32.65. % Cl calculated: 33.02.

(128) 2-chloro-2-methyl-3-(2-chlorophenyl)propanol (b.p.$_{0.01}$.130° C.); yield: 25%; % Cl found: 31.70. % Cl calculated: 32.4.

(129) 1,2-dichloro-2-methyl-3-(3-chloro-o-tolyl)propane (b.p.$_{0.1}$.116°–120° C.); yield: 22%; % Cl found: 41.70. % Cl calculated: 42.3.

(130) 3-chloro-3-methyl-4-(2,4,5-trichlorophenyl)butan-2-one (b.p.$_{0.5}$.136°–138° C.); yield: 70%; % Cl found: 46.5. % Cl calculated: 47.33.

(131) 3-chloro-3-methyl-4-(3-chloro-o-tolyl)butan-2-one (b.p.$_{0.05}$.118°–120° C.); yield: 76%; % Cl found: 28.51 % Cl calculated: 29.98.

(132) 3-chloro-3-methyl-4-(2-chlorophenyl)butan-2-one (b.p.$_{0.6}$.125°–130° C.); yield: 80%; % Cl found: 30.1. % Cl calculated: 30.73.

(133) 3-chloro-3-methyl-4-(4-carboxyphenyl)butan-2-one (m.p. 132°–133° C.); yield: 45%; % Cl found: 15.07. % Cl calculated: 15.67.

(134) 2-chloro-3-(2-chlorophenyl)propyl 3-carballyloxypropionate (b.p.$_{0.01}$.172°–175° C.); yield: 50%; % Cl found: 20.3. decomposition % Cl calculated: 20.58.

(135) 2-chloro-3-(6-chloro-o-tolyl)propyl 3-carballyloxy acrylate (b.p.$_{0.1}$.180°–185° C.); yield: 20%; % Cl found: 19.70. % Cl calculated: 19.18.

(136) 2,3-epoxypropyl 2-chloro-3-(2,5-dichlorophenyl)-propionate (b.p.$_{0.1}$.200°–204° C.); yield: 75%; % Cl found: 35.60. % Cl calculated: 35.91.

(137) 2-methyl-3-chloro-4-(2-chlorophenyl)butan-2-ol (b.p.$_{0.2}$.132°–135° C.); yield: 30%; % Cl found: 29.10. % Cl calculated: 30.4.

(138) 1-ethoxy-1-chloro-2-(3-chloro-o-tolyl)ethane (b.p.$_{0.1}$.135°–140° C.); yield: 15%; % Cl found: 31.5. % Cl calculated: 30.47.

(139) α-chloro-α-methyl-β-(3-chloro-o-tolyl)propionaldehyde (b.p.$_{0.01}$.98°–100° C.); yield: 75%; % Cl found: 30.57. % Cl calculated: 30.73.

It is important to notice that in the process making the subject matter of the invention, the alkanoic acid is present during the diazotization step and that the diazonium chloride thus formed is then reacted with the olefinic compound in a solvent.

From the practical point of view, it has been considered as advantageous to use the alkanoic acid already in the first step (i.e. the diazotization); this may be understood easily and without further explanation if it is considered that by working in this manner the solution of diazonium salt may be collected without being obliged to add the alkanoic acid before passing to the second step.

The disclosure given hereinabove by Table 1 experiment IX clearly shows that the use of sodium acetate in the reaction does not produce good results and that a high amount of by-products and residue is formed.

Experiments made in regard of examples 29, 77 and 82 have proved the superiority of the process of the invention from the point of view of the output.

EXAMPLE 29

| (C.A.70 10696 w) | | |
|---|---|---|
| output | classic method | 28% |
| | application process | 72% |

EXAMPLE 77

| (C.A. 51 8688 g) | | |
|---|---|---|
| output | classic method | 26.7% |
| | application process | 63% |

EXAMPLE 82

| (C.A. 50 3293 h) | | |
|---|---|---|
| output | classic method | 41% |
| | application process | 70% |

The improved yield and shortened reactiom time are the main results of the process.

Moveover it renders possible to prepare a great number of chemicals with various structures, based on the arylation of olefins.

For example all arylated derivatives according to the process have a side chain of at least two carbon atoms provided in β with regard to the arene nucleus, with a chlorine atom which can easily be hydrolyzed.

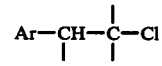

This property of the chlorine in β-position may be used to go further with the process synthesis and to prepare new derivatives either by elimination of HCl in the lateral chain, either in replacing the β-chlorine by a hydrogen or other groups.

In the case of arylation of diene compounds, the reactive chlorine is bonded to the gamma-carbon of the side chain.

We claim:

1. A process for the haloarylation of an olefinic compound by addition of an aryl group and a halo group to a double bond of said olefinic compound which consists essentially of the steps of reacting an arylamine with sodium nitrite in an aqueous acidic solution consisting essentially of a halohydric acid and a lower alkanoic acid at about 0° C. to 4° C. to form a solution of an aryldiazonium halide and reacting said aryldiazonium halide solution with an olefinic compound in acetone as a solvent at a temperature of about 0° to 40° C. in the presence of a catalytically effective amount of a copper halide, wherein the amount of alkanoic acid is about 15 to 37% by volume of the total solvents used and the arylation reaction begins at a pH = 0 to 1, wherein the aryldiazonium halide has the formula:

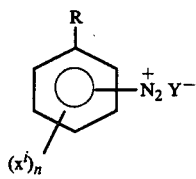

wherein R is a hydrogen atom or a lower alkyl, trifluoromethyl, hydroxy, lower alkoxy, lower alkylthio or di-(lower alkyl)-amino group or a phenyl, phenoxy or phenylthio group, in which the phenyl nucleus may be substituted by halogen, $CF_3$, $NO_2$, CN, COOH or $-CH_2-CHCl-CN$;

$X^i$ is a hydrogen atom or a halogen atom, a lower alkyl, nitro, cyano or carboxy group, or R and $X^i$ together denote a tri-atomic or tetra-atomic chain which may or may not be saturated and which together with the phenyl nucleus form a bicyclic radical of the naphthalene or benzoheterocyclic series, $Y^-$ is a halide ion and n is a whole number from 1 to 4, and wherein the olefinic compound has the formula

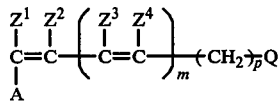

wherein $Z^1$, $Z^2$, $Z^3$ and $Z^4$ which may be the same or different are each a hydrogen or halogen atom or a lower alkyl radical.

A is a hydrogen atom or a lower alkyl radical,

Q is a hydrogen or halogen atom or a cyano, nitro, hydroxy or trifluoromethyl group or a heterocyclic radical or an alkyl, epoxyalkyl, alkoxy, alkenoxy, alkylsulfonyl, alkenylsulfonyl, alkylamino, alkenylamino, or carbalkoxy wherein any alkyl or alkenyl chain may be substituted by halogen, hydroxy or carboxy; aryl, aryloxy, or aryloxycarbonyl in which the aryl radical may be substituted by halogen, trifluoromethyl, alkyl, alkoxy, alkenyloxy, nitro or carboxy groups; or an acyl, acyloxy, cycloalkyl or cycloalkenyl group;

m is 0 or 1 and p is 0, 1 or 2.

2. The process according to claim 1 wherein the reaction between the aryldiazonium halide solution and the olefinic compound is effected at about 0° to 25° C.

3. The process according to claim 1 in which the halohydric acid is hydrochloric acid.

4. The process according to claim 1 in which the alkanoic acid is acetic acid and the copper halide is cuprous chloride.

5. The process according to claim 3 in which the alkanoic acid is acetic acid and the copper halide is cuprous chloride.

6. In a process for effecting haloarylation of olefins by reacting in a first step an arylamine with sodium nitrite in a halohydric acid solution to form a solution of aryldiazonium halide and then in a second step without isolating said aryldiazonium halide from its solution, reacting said aryldiazonium halide with an olefin in the presence of a catalytically active amount of copper halide, the improvement which consists in beginning said second step at a pH = 0 to 1 in the presence of an alkanoic acid in the amount of about 15 to 37% by volume of the total solvents used.

7. The process according to claim 6, wherein the alkanoic acid is added in said first step and is selected from the group consisting of formic, acetic and propionic acid.

8. The process according to claim 6 wherein the copper halide is cuprous chloride and said second step is effected at a temperature of from 0° to 40° C.

9. The process according to claim 6 wherein the aryldiazonium salt has the formula,

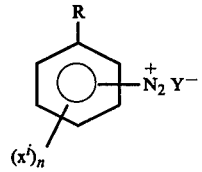

wherein R is a hydrogen atom or a lower alkyl, trifluoromethyl, hydroxy, lower alkoxy, lower alkylthio or di(lower alkyl)-amino group or a phenyl, phenoxy or phenylthio group, in which the phenyl nucleus may be substituted by halogen, $CF_3$, $NO_2$, CN, COOH or $-CH_2-CHCl-CN$;

$X^i$ is a hydrogen or halogen atom, a lower alkyl, nitro, cyano or carboxy group, or R and $X^i$ together denote a tri-atomic or tetra-atomic chain which may or may not be saturated and which together with the phenyl nucleus to which they are attached form a bicyclic radical of the naphthalene series, $Y^-$ is a halide ion, and n is a whole number from 1 to 4.

10. The process according to claim 9 wherein the olefin has the formula

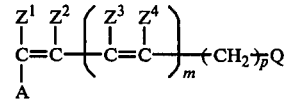

wherein, $Z^1$, $Z^2$, $Z^3$ and $Z^4$ which may be the same or different are each a hydrogen atom or a lower alkyl radical, A is a hydrogen atom or a lower alkyl radical, Q is a hydrogen or halogen atom, or a cyano, nitro, hydroxy or trifluoromethyl group or a heterocyclic radical, or an alkyl, epoxyalkyl, alkoxy, alkenoxy, alkylsulfonyl, alkenylsulfonyl, alkylamino, alkenylamino, carboalkoxy, aryl, aryloxy, aryloxycarbonyl, acyl, acyloxy, cycloalkyl or cycloalkenyl group, wherein any alkyl or alkenyl chain may be substituted by halogen, hydroxy or carboxy, and any aryl group may be substituted by halogen, trifluoromethyl, alkyl, alkoxy, alkenyloxy, nitro or carboxy groups m is 0 or 1 and p is 0, 1 or 2.

11. The method according to claim 1 wherein the olefinic compound is acrylonitrile and the arylamine is 3-chloro-o-toluidine.

12. The method according to claim 1 wherein the olefinic compound is selected from the group consisting of acrylonitrile, α-chloroacrylonitrile, methacrylonitrile, vinylacetonitrile and crotonic nitrile.

* * * * *